Figure 1:
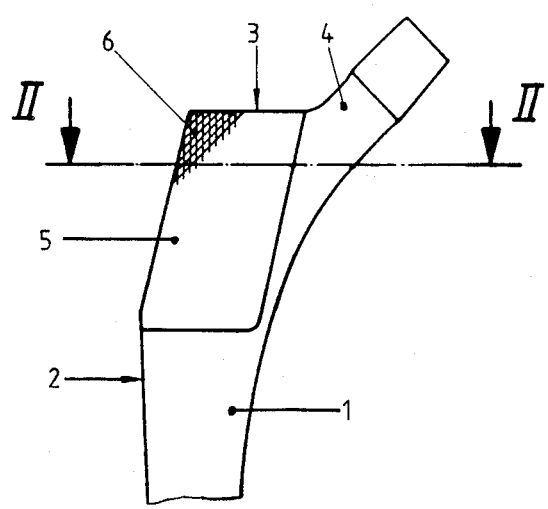

United States Patent [19]

Frey et al.

[11] Patent Number: 4,883,492
[45] Date of Patent: Nov. 28, 1989

[54] METAL BONE IMPLANT

[75] Inventors: Otto Frey, Winterthur; Rudolf Koch, Berlingen, both of Switzerland

[73] Assignee: Sulzer Brothers Limited, Winterthur, Switzerland

[21] Appl. No.: 198,397

[22] Filed: May 26, 1988

[30] Foreign Application Priority Data

Jun. 23, 1987 [CH] Switzerland ................ 2363/87

[51] Int. Cl.⁴ .............................................. A61F 2/36
[52] U.S. Cl. ...................................... 623/23; 623/16; 623/18; 623/20; 623/22
[58] Field of Search ............... 623/16, 18, 20, 22, 623/23

[56] References Cited

U.S. PATENT DOCUMENTS

| D. 248,771 | 8/1978 | Groth, Jr. et al. | 623/20 |
|---|---|---|---|
| 4,007,495 | 2/1977 | Frazier | 623/20 |
| 4,718,915 | 1/1988 | Epinette | 623/23 |
| 4,718,916 | 1/1988 | Morscher | 623/23 |
| 4,778,469 | 10/1988 | Lin et al. | 623/20 X |

FOREIGN PATENT DOCUMENTS

| 0196258 | 10/1986 | European Pat. Off. | 623/23 |
|---|---|---|---|
| 0217034 | 4/1987 | European Pat. Off. | 623/23 |

Primary Examiner—Richard J. Apley
Assistant Examiner—N. Paul
Attorney, Agent, or Firm—Kenyon & Kenyon

[57] ABSTRACT

The implanted is constructed with a metal base element and a plastic part which is elastically mounted on the base element and carries a metal grid structure for the ingrowth of bone tissue. The elastic mounting is provided by a prop which extends from a body portion of the plastic part into a depression in the base element. The prop is received in the depression with lateral play to not only hold the mutually facing surfaces of the base element and plastic part from each other but to permit lateral play. The floating suspension permits inevitable micromovements between the metal implant and the plastic part to be absorbed and not transmitted directly to the bone tissue which grows into the metal grid structure.

7 Claims, 1 Drawing Sheet

U.S. Patent  Nov. 28, 1989  4,883,492

METAL BONE IMPLANT

This invention relates to a metal bone implant. More particularly, this invention relates to a hip joint implant.

Heretofore, are various types of implants have been known wherein a molded plastic part is mounted on a metal part in order to carry a grid structure for the ingrowth of tissue. For example, published European Patent Application No. 0 217 034 and published European Patent Application No. 0 196 258 describe shanks for a cementless anchoring of a femur head prosthesis wherein a molded plastic part is applied to the proximal region and covered on the outside with a wire grid for the ingrowth of tissue.

However, it has been found that, under changing loads on an implant, micromovements occur between the implant and the surrounding bone due to different elasticity properties. In the case of the above noted constructions, the micromovements are transmitted directly to the bone tissue grown into the wire grid. As a result, damage may occur to the tissue with a consequent loosening of the implant.

Accordingly, it is an object of the invention to suppress the transmission of micromovements from an implant to tissue growing into a grid on the implant.

It is another object of the invention to provide for a reliable inplantation of a bone implant.

Briefly, the invention provides a bone implant which is comprised of a metal based element, a plastic part which is elastically mounted on the base element and a metal grid structure mounted on the plastic part for the ingrowth of bone tissue.

In order to provide for the elastic mounting of the plastic part, the metal base element is provided with at least one depression while a body portion of the plastic part is spaced from the base element by at least one prop which extends from the body portion into the depression of the base element with a lateral clearance therein. This prop serves to support the body portion in elastically displaceable manner relative to the base element. In addition, at least one elastic projection extends from the plastic body portion to against the base element to prevent canting of the plastic part.

With this construction, there is no rigid connection between the metal base element and the plastic part. Due to the elasticity of the projections and the play in the mounting of the prop, the plastic part "floats" so to speak on the surface of the base element. Consequently, micromovements of the base element are not transmitted to the plastic part and, hence, not to the bone tissue growing into the metal grid structure.

The prop or props which may be constructed, for example as stays or ribs are primarily responsible for the spacing of the opposed surfaces of the base element and plastic part relative to each other. The projections serve to prevent a mutual canting of the two parts and, to a certain extent guide the relative mvements of the parts. These projections may also be formed as nub-like discrete elements of any suitable cross-section or as ribs.

In order to prevent a growing in of bone tissue into the gap between the base element and the plastic part, the spacing between these two parts is at most one millimeter. In this respect, it is known that tissue growing into a gap or groove will advance only to depth which, very roughly in a first approximation, corresponds to the gap width. Further the accretion of tissue at the edge of the gap can be minimized by making the surfaces of the base element and plastic part smooth.

Figure 2:
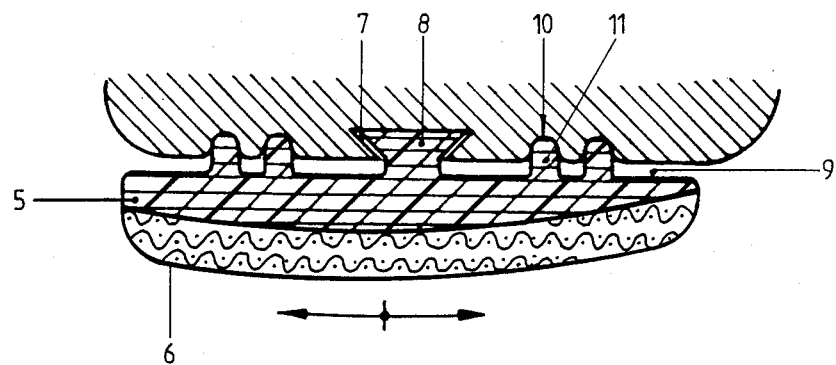

These and other objects and advantages of the invention will become more apparent from the following detailed description taken in conjunction with the accompanying drawings wherein:

FIG. 1 schematically illustrates a shank for a hip joint implant constructed in accordance with the invention;

FIG. 2 illustrates a view taken on line II—II of FIG. 1.

Referring to FIG. 1, the bone implant is in the form of a hip joint implant, for example for a femur head prosthesis. As indicated, the base element includes a blade-like shank 1 which tapers in the distal direction and which has a lateral narrow side 2 which is continued at the proxmmal end over a horizontal shoulder 3 to a neck 4. In addition, the shank 1 carries a molded plastic part 5 in a known manner in a proximal region. This plastic part 5 may be of any known plastic, such as polyethylene of medical quality. In addition, the plastic part 5 is covered on the outer surface with a metal grid structure, for example a multi-ply wire grid 6 of titanium or a titanium alloy for the ingrowth of tissue in order to anchor the shank 1.

Referring to FIG. 2, the plastic part 5 is elastically mounted in the blade-like shank 1. To this end, the shank 1 is provided with a depression 7 in the form of a dovetail-shaped guide groove which extends parallel or obliquely to the longitudial axis of the shank 1. In addition, the plastic part 5 has a main body portion from which at least one prop 8 extends into the depression 7 with a lateral clearance therein. The "height" of the prop 8 protruding from the surface of the plastic part 5 is such that a gap 9 results between the plastic part 5 and the base element 1.

As indicated in FIG. 2, the dimensions of the matching dovetail groove or depression 7 and the prop 8 are adapted to each other so that there is a lateral play which permits relative movements, indicated by a double arrow, between the plastic part 5 and the base element 1.

The plastic part 5 is also provided with a plurality of elastic projections 11 on opposite sides of the prop 8 which extend against the base element 1. In this respect, the base element 1 is provided with a plurality of recesses 10 to receive the projections 11. The projections 11 serve to guide the relative movements between the base element 1 and the plastic part 5. In addition, the projections 11 are dimensioned in their cross-sections relative to their height, depending on the plastic used for part 5, in such a way that the projections 11 are deformed elastically when relative movements occur between the base element 1 and the molded part 5. In the illustrated example, the recesses 10 are formed as concave flutes which extend parallel to the dovetail groove 7 while the projections 11 are in the form of ribs.

In order to minimize the accretion of tissue between the surfaces of the base element 1 and plastic part 5 which face each other, within the gap 9, the surfaces may be smooth, for example, polished.

Since it is known that the depth of growth of bone tissue into depressions or gaps is approximately as great as the gap width, the gap 9 is kept as small as possible. In practice, the gap width may be in the range from 0.1 to 1 millimeter.

The form of the depression 7 and the prop 9 as well as the form of the recesses 10 and the projections 11 may be varied in various ways. For example, stay—type props 8 and nub-like projections 11 permit not only relative movements in one dimension but also movements in any desired directions of a plane.

The invention thus provides an elastic mounting or suspension of a molded plastic part on a metal implant base element in such a way that micromovements between the base element and plastic parts are not transferred into the tissue growing into the metal grid structure mounted on the plastic part.

What is claimed is:

1. A hip joint implant comprising:
    a blade-like shank of metal having at least one depression therein;
    a plastic part having a body portion spaced from said shank at least one prop extending from said body portion into said depression with a lateral clearance therein to support said body portion in elastically displaceable manner relative to said shank and at least one elastic projection extending from said body portion to against said shank; and
    a metal grid structure mounted on said plastic part opposite said shank for ingrowth of bone tissue.

2. A hip joint implant as set forth in claim 1 wherein said shank and said plastic part have smooth surfaces facing each other.

3. A hip joint implant as set forth in claim 1 wherein said body portion of said plastic part is spaced from said shank by at most 1 millimeter.

4. A bone implant comprising;
    a metal base element having at least one depression therein;
    a plastic part having a body portion spaced from said base element at least one prop extending from said body portion into said depression with a lateral clearance therein to support said body portion in elastically displaceable manner relative to said base element and at least one elastic projection extending from said body portion to against said base element; and
    a metal grid structure mounted on said plastic part opposite said shank for ingrowth of bone tissue.

5. A bone implant as set forth in claim 4 wherein said depression is a groove and said prop is a rib slidably mounted therein.

6. A bone implant as set forth in claim 5 wherein said base element has a concave flute parallel to said groove and said projection of said plastic part is received in said flute.

7. A bone implant as set forth in claim 4 wherein said base element has a recess and said projection of said plastic part is received in said recess.

* * * * *

UNITED STATES PATENT AND TRADEMARK OFFICE
CERTIFICATE OF CORRECTION

PATENT NO. : 4,883,492

DATED : Nov. 28, 1989

INVENTOR(S) : Otto Frey, et al

It is certified that error appears in the above-identified patent and that said Letters Patent is hereby corrected as shown below:

```
In the Abstract, line 1 "implanted" should be -implant-
Column 1, line 6 ", are various" should be -, various-
Column 3, line 16 "shank at" should be -shank, at-
Column 4, line 8 "element at" should be -element, at-
```

Signed and Sealed this

Twentieth Day of November, 1990

Attest:

HARRY F. MANBECK, JR.

Attesting Officer

Commissioner of Patents and Trademarks